United States Patent
Mower

(10) Patent No.: US 11,406,834 B2
(45) Date of Patent: Aug. 9, 2022

(54) CROSSOVER ADAPTER AND CROSSOVER LEAD

(71) Applicant: Morton M. Mower, Denver, CO (US)

(72) Inventor: Morton M. Mower, Denver, CO (US)

(*) Notice: Subject to any disclaimer, the term of this patent is extended or adjusted under 35 U.S.C. 154(b) by 240 days.

(21) Appl. No.: 16/038,660

(22) Filed: Jul. 18, 2018

(65) Prior Publication Data

US 2019/0083799 A1 Mar. 21, 2019

Related U.S. Application Data

(60) Provisional application No. 62/560,857, filed on Sep. 20, 2017.

(51) Int. Cl.
| | | |
|---|---|---|
| *A61N 1/375* | (2006.01) | |
| *A61N 1/05* | (2006.01) | |
| *A61N 1/36* | (2006.01) | |
| *A61N 1/04* | (2006.01) | |
| *A61N 1/362* | (2006.01) | |

(52) U.S. Cl.
CPC ......... *A61N 1/37512* (2017.08); *A61N 1/056* (2013.01); *A61N 1/36114* (2013.01); *A61N 1/3752* (2013.01); *A61N 1/0416* (2013.01); *A61N 1/3627* (2013.01)

(58) Field of Classification Search
None
See application file for complete search history.

(56) References Cited

U.S. PATENT DOCUMENTS

| | | | | |
|---|---|---|---|---|
| 5,222,506 A | * | 6/1993 | Patrick | A61N 1/056 607/126 |
| 7,563,141 B2 | * | 7/2009 | Alexander | A61N 1/0529 439/669 |
| 2010/0324617 A1 | * | 12/2010 | Ong | A61N 1/056 607/9 |
| 2013/0296965 A1 | * | 11/2013 | Mokelke | A61N 1/056 607/44 |

* cited by examiner

*Primary Examiner* — Erica S Lee
(74) *Attorney, Agent, or Firm* — Oblon, McClelland, Maier & Neustadt, L.L.P.

(57) ABSTRACT

An adapter includes a first connector, a second connector, and a circuit that reverses a polarity of a signal received at the first connector. Moreover, a lead includes a connector including a cathode terminal and an anode terminal, an electrode including a tip and a ring, and a circuit that connects the anode terminal of the connector to the tip of the electrode and that connects the cathode terminal of the connector to the ring of the electrode.

9 Claims, 5 Drawing Sheets

CROSSOVER ADAPTER AND CROSSOVER LEAD

CROSS-REFERENCE TO RELATED APPLICATIONS

This application claims priority to U.S. Provisional Application No. 62/560,857 filed Sep. 20, 2017, the entire contents of which is incorporated herein by reference.

BACKGROUND

Field of the Invention

The present disclosure is directed to leads for cardiac pacing, and specifically to an adapter and leads for pacing with reverse polarity.

Description of the Related Art

Conventional cardiac pacing uses cathodal polarity to stimulate the heart. While small amounts of anodal currents are sometimes used to reverse charge accumulation in electrodes, improving sensing, there has not been clinical interest in stimulating the heart with anodal polarity. This lack of interest may be because cathodal polarity pacing may be deemed to be sufficiently effective in treating heart ailments. However, pacing with cathodal polarity is still associated with a degree of morbidity and mortality because of hitherto unrecognized slowing of conduction and reduction of contractility.

Perhaps because of the prevalent use of cathodal polarity, conventional cardiac pacers typically output pacing signals in only one polarity, cathodal, and have connectors designed to accept lead connection in only one way. This makes it extremely difficult, if not impossible, to use conventional cardiac pacers to deliver anodal polarity pacing.

Recently, there is significant evidence that biphasic waveforms with an anodal pulse that precedes a cathodal pulse can improve conduction speeds and contractility because of the increased cell membrane potential prior to stimulation. Therefore, there is a need for an adaptor that allows the generation of anodal polarity from a conventional cardiac pacer.

SUMMARY OF THE INVENTION

In a first exemplary aspect, an adapter includes a first connector, a second connector, and a circuit that reverses a polarity of a signal received at the first connector.

The circuit of the adapter may include a first wire that connects a cathode terminal of the first connector to an anode receptacle of the second connector, and a second wire that connects an anode terminal of the first connector to a cathode receptacle of the second connector.

In the adapter, the first connector may connect in only one orientation.

In the adapter, the second connector may connect in only one orientation.

The adapter may also be implanted in a patient.

The adapter may also be formed as a single unit encased in one of a plastic, a silicone, a polymer, or a metal.

The adapter may also include a pc board on which the first and second connectors are mounted, and the first and second wires of the adapter are traces on the pc board.

The adapter may be a lead extender.

In another exemplary embodiment, a lead includes a connector including a cathode terminal and an anode terminal, an electrode including a tip and a ring, and a circuit that connects the anode terminal of the connector to the tip of the electrode and that connects the cathode terminal of the connector to the ring of the electrode.

the circuit of the lead may include a first wire that connects the cathode terminal of the connector to the ring of the electrode, and a second wire that connects the anode terminal of the connector to the tip of the electrode.

The connector of the lead may also connect in only one orientation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
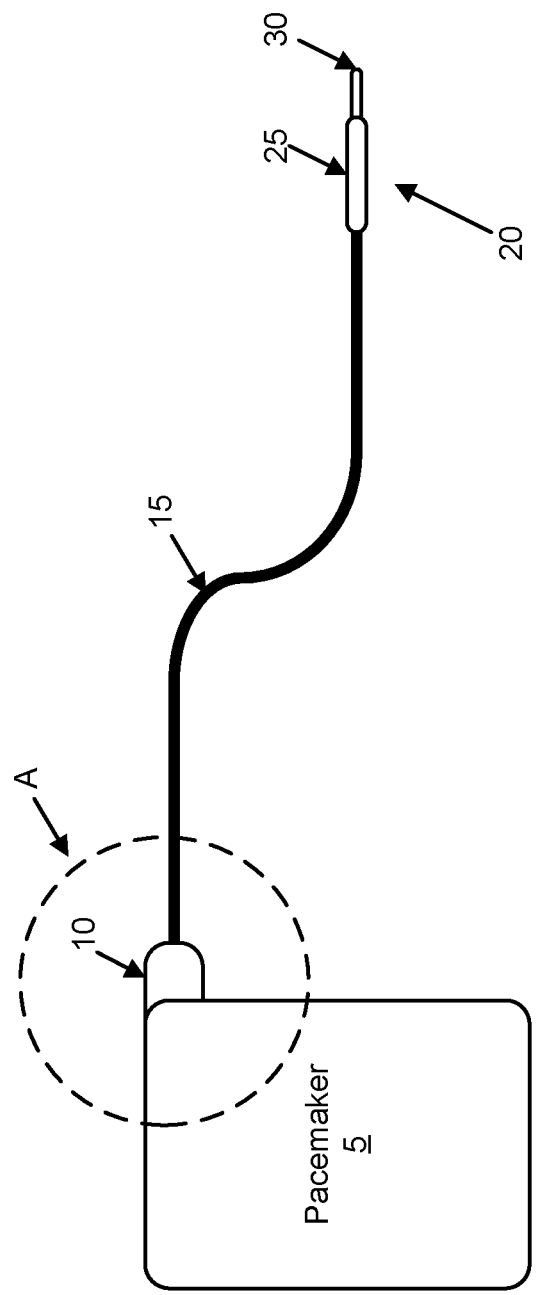
FIG. 1 is a diagram of a cardiac pacer with a lead connected thereto according to exemplary aspects of the present disclosure.

Referring now to the drawings, wherein like reference numerals designate identical or corresponding parts throughout the several views, FIG. 1 is a diagram of a cardiac pacer and lead according to exemplary aspects of the present disclosure. In FIG. 1, the cardiac pacer 5 may generate only cathodal polarity waveforms, or may generate a biphasic waveform in which the first part of the waveform is cathodal and the second part is anodal in order to remove charge from the electrode 20 to improve sensing. The cardiac pacer 5 may be implantable and therefore battery powered, or may be external to the patient and be either battery powered or powered from an external source, such as the main power grid. As can be appreciated, the cardiac pacer 5 may generate pacing pulses to address a wide variety of cardiac passing issues.

Connected to the cardiac pacer 5 is a lead that includes a lead connector 10, a lead cable 15, and an electrode 20. Thought the lead is shown as having only one electrode 20, a lead with multiple electrodes may also be used without departing from the scope of the present advancements. The cardiac pacer 5 may monitor predetermined cardiac parameters based on signals sensed by the electrode 20 and provided to the cardiac pacer 5 by the lead. The cardiac pacer 5 may also monitor cardiac parameters via signals sensed by other electrodes (not shown) in addition to, or instead of, the signals sensed by the electrode 20. Of course, the cardiac pacer 5 may also be pre-programmed to deliver a particular series of stimulating pulses without monitoring any cardiac parameters as one of ordinary skill would recognize.

Figure 2:
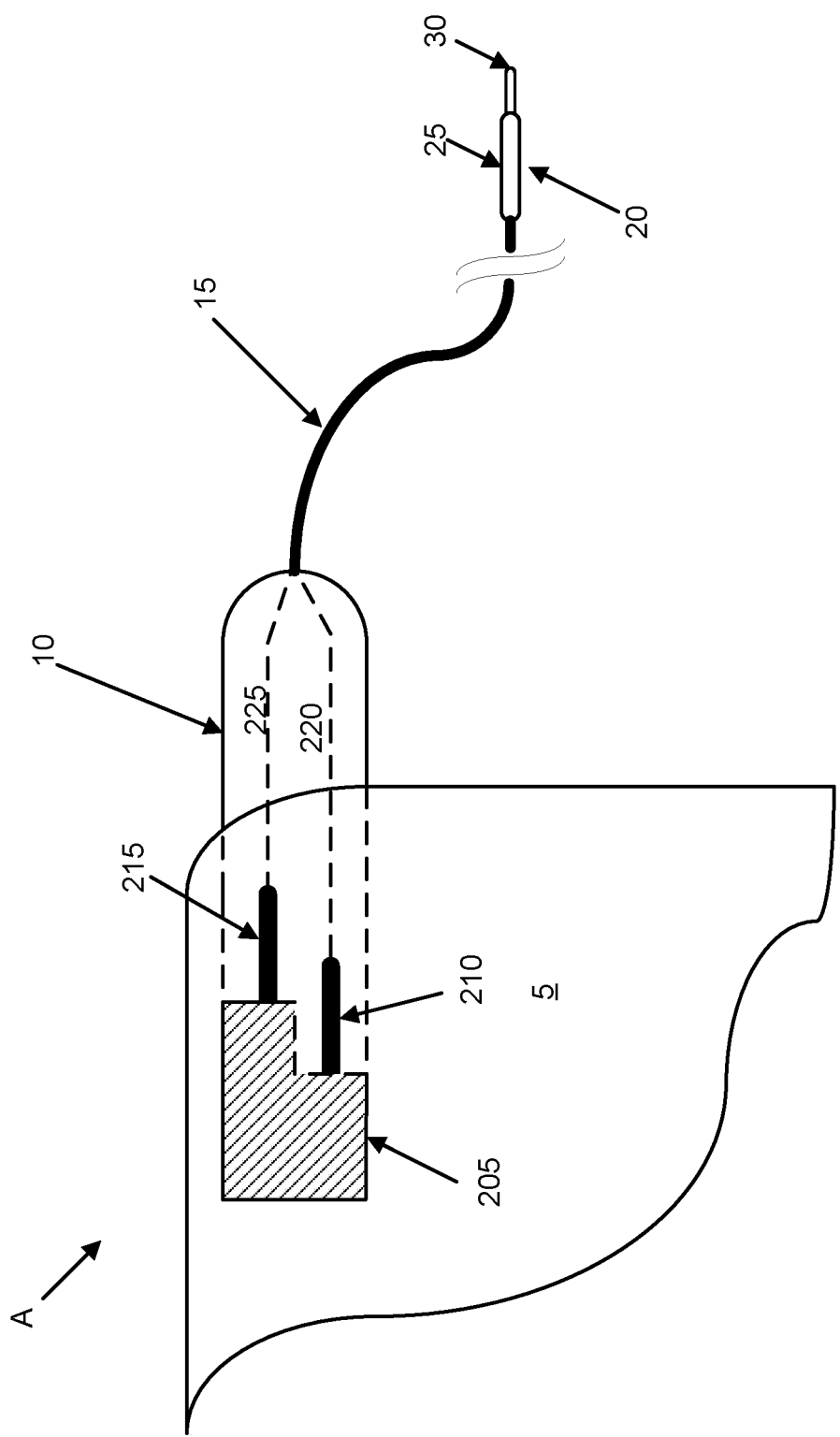
FIG. 2 is a detail diagram of the connection between the cardiac pacer and the lead according to exemplary aspects of the present disclosure.

In order to deliver a pacing signal, the cardiac pacer 5 provides a signal to the electrode 20 via the lead and lead cable. In order to do this, the lead is connected to the cardiac pacer 5 by at least two wires as illustrated in FIG. 2. In FIG. 2, the lead connector 10 plugs into a connector 205 of the cardiac pacer 5. Though the connector 205 of the cardiac pacer 5 is illustrated as residing within the cardiac pacer 5, the connector may also be flush with the exterior surface of the cardiac pacer 5 or may even partially protrude from the cardiac pacer 5. The connector 205 may also be wholly outside the cardiac pacer 5 and connected thereto by a cable or wires. As such, the particular placement of the connector 205 illustrated in FIG. 2 is merely exemplary and is not limiting upon the present disclosure.

As can be seen from FIG. 2, the connector 205 is keyed so that the lead connector 10 can only be connected to the connector 205 in one orientation. For example the connector 205 has one side longer than another in order to form an "inverted step" to which the lead connector 10 can only attach when oriented as "step" to compliment the inverted step of the connector 205. The connector 205 may also have other designs to force the connector 10 to connect to it in a single orientation as one of ordinary skill would recognize.

The lead connector 10 may include two pins 215 and 210 that respectively fit into receptacles (not shown) in the connector 205. In this case, the pin 215 corresponds to the cathode connection and the pin 210 corresponds to the anode connection. However, this can be reversed as one of ordinary skill would recognize. Each pin 210, 215 is connected to a wire 225, 220 that, in turn, connects to the electrode 20. In conventional leads, the pin 215, which corresponds to the cathode connection, is connected to the tip 30 of the electrode 20 by the wire 225. The pin 210, which corresponds to the anode connection, is connected to the ring 25 of the electrode 20 by the wire 220. As can be appreciated, the tip 30 and ring 25 of the electrode 20 are electrically isolated from each other.

Since the connector 205 of the cardiac pacer 5 is hardwired in a particular polarity, and the lead connector 10 can connect to the connector 205 in only one way, typical leads are only able to deliver pacing pulses that are cathodal (i.e., the cathode is connected to the tip 30 and the anode is connected to the ring 25 of the electrode 20). Even if the cardiac pacer 5 is able to generate a biphasic waveform whose second half is a small anodal pulse, the polarity orientation remains fixed with the cathode at the tip 30 and the anode at the ring 25 of the electrode 20.

Figure 3:
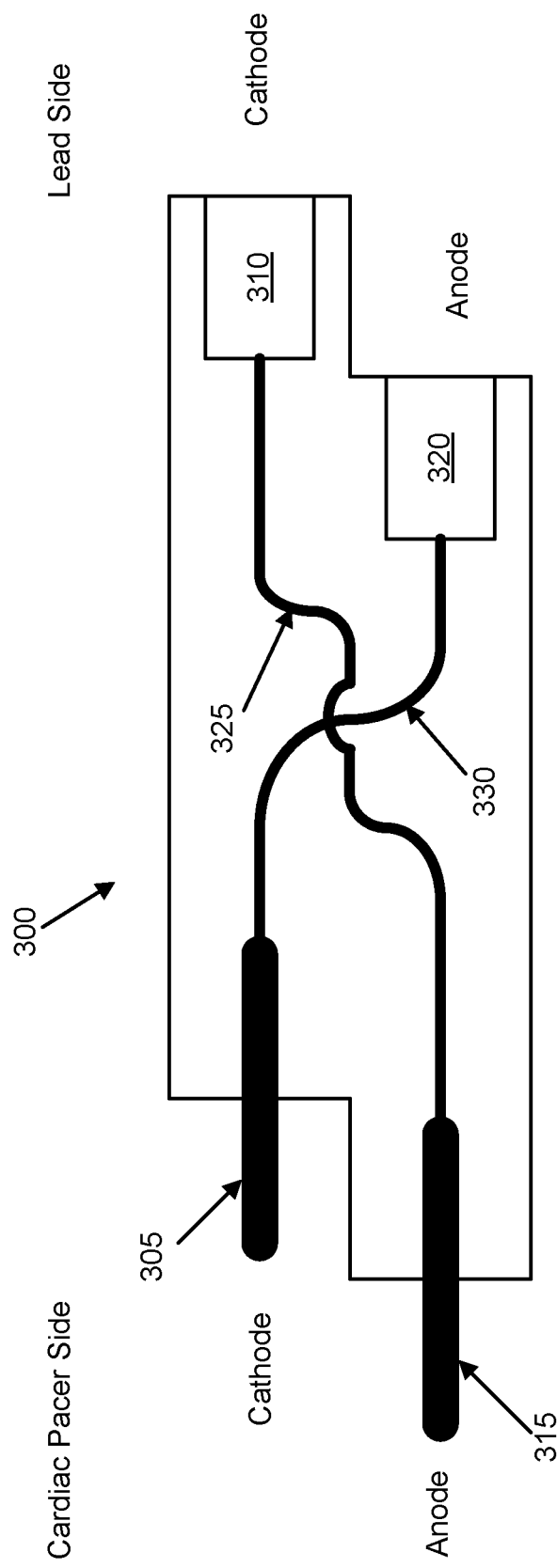
FIG. 3 is a diagram of an adapter according to exemplary aspects of the present disclosure.

FIG. 3 illustrates an adapter 300 according to exemplary aspects of the present disclosure. The adapter 300 includes two pins 305 and 315 to connect to the connector 205 of the cardiac pacer 5. The profile of the adapter 300 is such that it matches the inverted step profile of the connector 5. Thus, from the perspective of the cardiac pacer 5, the pin 305 is the cathode connection pin and the pin 315 is the anode connection pin. Pin 305 is connected to the receptacle 320 which receives one connection pin from the lead connector 10, and pin 315 is connected to the receptacle 310 which receives the other connection pin from the lead connector 10. Because the lead side of the adapter 300 has the same form factor as the connector 205 of the cardiac pacer 5, the lead connector 10 can only connect to the adapter 300 in one way. Thus the adapter "switches" the connections such that the cathode polarity signal received by the pin 305 is provided via the wire 330 to the ring 25 of the electrode 20 of the lead via the receptacle 320. Likewise, the anode polarity signal is provided to the tip 30 of the electrode 20 of the lead via the receptacle 310. Therefore, the adapter 300 effectively reverses the polarity of the signals generated by the cardiac pacer 5 allowing anodal pacing pulses to be administered. In the case of biphasic pacing, the adapter 300 allows the leading pulse to be anodal and the trailing pulse to be cathodal.

In FIG. 3 a "step" form factor is used to indicate that the respective connectors fit together in only one orientation. However, other form factors are also possible. For example, instead of separate pins, a plug, such as an RCA plug in which the cathode connection is made by the tip and the anode connection is made by the sleeve, may be used. A plug that is divided into separate electrical contacts by an insulating material may also be used. Thus, the exact manner in which connection in a single orientation is ensured is not limiting on the present disclosure.

Moreover, the adaptor 300 may be formed as a single unit, such as a pc board with traces serving as the wires 325 and 330. In this case the entire assembly may be encased in plastic, silicone, or other polymer. In the case that the cardiac pacer 5 is external to the body, the adapter 300 may also be enclosed in a metallic case. Other case materials are also possible as one of ordinary skill would recognize.

Figure 4:
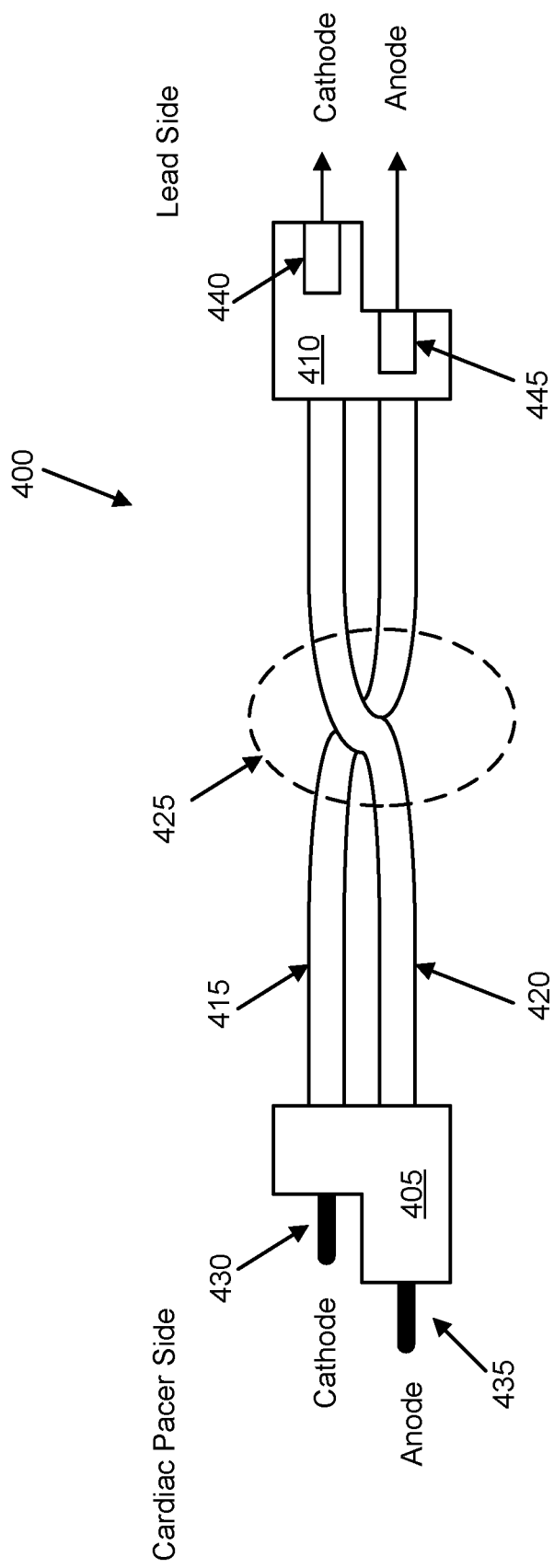
FIG. 4 is a diagram of another adapter according to exemplary aspects of the present disclosure.

FIG. 4 illustrates another adapter 400 according to exemplary aspects of the present disclosure. The adapter 400 of FIG. 4 includes a cardiac pacer side connector 405 that has a pin 430 to make the cathode connection with the cardiac pacer 5, and a pin 435 to make the anode connection with the cardiac pacer 5. The adapter 400 also includes a lead side connector 410 that includes a receptacle 440 that connects make the cathode connection with the lead (i.e., the connection to the tip 30 of the electrode 20), and a receptacle 445 to make the anode connection with the lead (i.e., the connection to the ring 25 of the electrode 20). The connectors 405 and 410 are connected by wires 415 and 420. For example, the wire 415 is connected to the cathode pin 430 of the connector 405 and to the anode receptacle 445 of the connector 410. The wire 420 is connected to the anode pin 435 of the connector 405 and to the cathode receptacle of the connector 410. Thus, the wires 415 and 420 are effectively crossed at 425. As can be appreciated, the crossing point 425 does not have to be in the middle of the wires 415 and 420, and may be closer to either of the connectors 405 and 410 without departing from the scope of the present disclosure.

The adapter 400 can be regarded as a lead extender and the wires 415 and 420 may be any length required without limitation. The wires 415 and 420 may also be encased in a sheath. The connectors 405 and 410 may also be replaced by any of the connectors discussed above with reference to FIG. 3.

Figure 5:
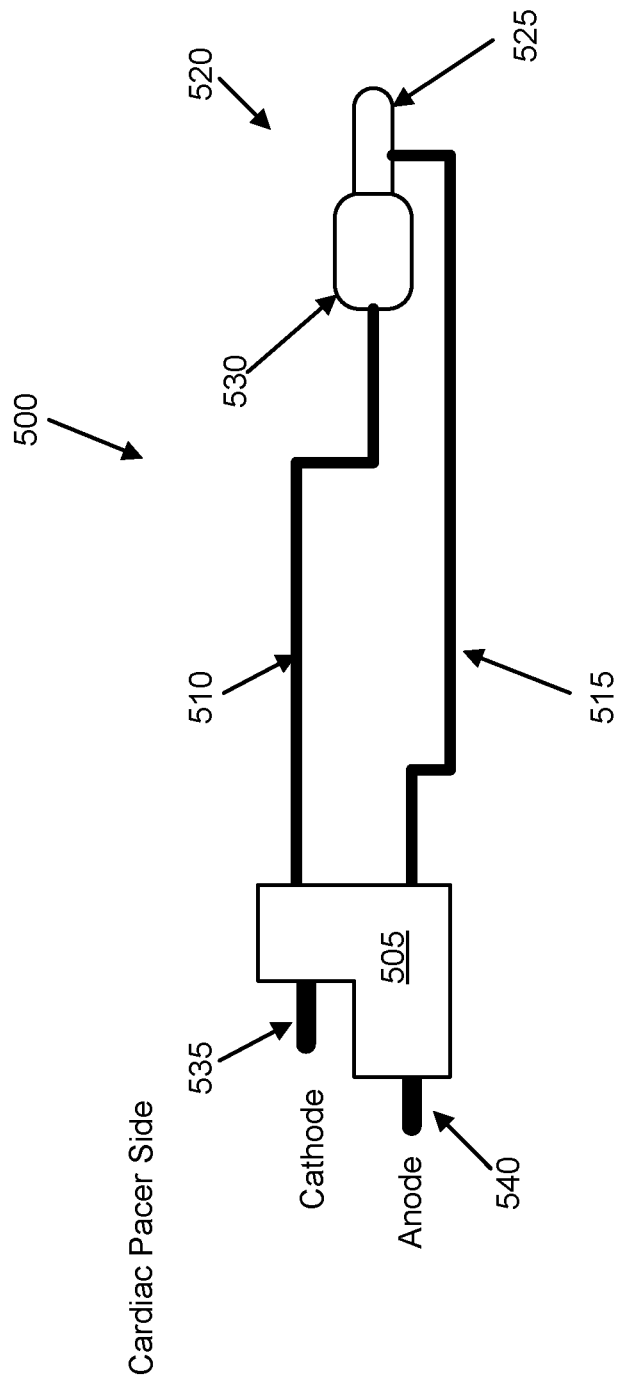
FIG. 5 is a diagram of lead accord to exemplary aspects of the present disclosure.

Next a lead 500 according to exemplary aspects of the present disclosure is described with reference to FIG. 5. The lead 500 includes a connector 505 to connect to the connector 205 of the cardiac pacer 5. The connector 505 includes a cathode pin 535 to connect to the cathode receptacle of the connector 205 as discussed above with reference to FIGS. 3-5. The connector 505 also includes an anode pin 540 to connect to the anode receptacle of the connector 205 (as also discussed above). Wire 510 connects the cathode pin 535 to the ring 530 of the electrode 520 of the lead 500. Wire 515 connects the anode pin 540 to the tip 525 of the electrode 520. In this way the anode side of the signal generated by the cardiac pacer 5 is delivered to the tip 525 of the electrode 520 and the cathode side of the signal is delivered to the ring 530. In other words, the polarity of the signal generated by the cardiac pacer 5 is reversed by the lead 500.

The above discussed assumes that the cardiac pacer 5 generates cathodal signals or biphasic signals with leading cathodal pulses. However, the advancements described in the present disclosure can also be used to reverse the polarity of signals generated by a cardiac pacer that generates anodal signals or biphasic signals with leading anodal pulses. Moreover, the drawings in this application are made to aid in the understanding of the present advancements, but are merely exemplary and are not to scale. Obviously, numerous modifications and variations of the present invention are possible in light of the above teachings. It is therefore to be understood that within the scope of the appended claims, the invention may be practiced otherwise than as specifically described herein.

The invention claimed is:

1. An adapter for a lead, the adapter comprising:
a first step-shaped connector having a first step and a second step in a staggered configuration;
two terminal conductors disposed on the first connector, each of the first step and the second step of the first connector including only one of the two terminal conductors;
a second step-shaped connector having a third step and a fourth step in a staggered configuration, the third step being a first predetermined distance from the first step, the fourth step being a second predetermined distance from the second step, the first and second predetermined distances being equal;
two receptacle conductors disposed on the second connector, each of the third step and the fourth step of the second connector including only one of the two receptacle conductors; and
a circuit configured to connect to the first step-shaped connector and to the second step-shaped connector to reverse a polarity of a signal received at the first step-shaped connector and to provide the signal received at the first step-shaped connector, in reverse polarity, to the second step-shaped connector.

2. The adapter according to claim 1, wherein the circuit includes:
a first wire configured to connect a cathode terminal conductor of the two terminal conductors of the first step-shaped connector to an anode receptacle conductor of the two receptacle conductors of the second step-shaped connector; and
a second wire configured to connect an anode terminal conductor of the two terminal conductors of the first step-shaped connector to a cathode receptacle conductor of the two receptacle conductors of the second step-shaped connector.

3. The adapter according to claim 1, wherein the adapter is configured to be implanted in a patient.

4. The adapter according to claim 1, wherein the adapter is formed as a single unit encased in one of a plastic, a silicone, a polymer, or a metal.

5. The adapter according to claim 2, further comprising a printed circuit (pc) board on which the first and second step-shaped connectors are mounted, wherein the first and second wires are traces on the pc board.

6. The adapter according to claim 1, wherein the adapter is a lead extender.

7. The adapter according to claim 1, wherein the adapter is connected between a cardiac pacer and a cardiac lead having an electrode, and the adapter provides a cathodal output of the cardiac pacer to a ring of the electrode and an anodal output of the cardiac pacer to a tip of the electrode.

8. The adapter according to claim 7, wherein the first step-shaped connector is configured to connect to the cardiac pacer in only one orientation.

9. The adapter according to claim 8, wherein the second step-shaped connector is configured to connect to the cardiac lead in only one orientation.

* * * * *